United States Patent

Coates et al.

[11] Patent Number: 5,221,687
[45] Date of Patent: Jun. 22, 1993

[54] MEDICAMENTS

[75] Inventors: Ian H. Coates, Hertford; Alexander W. Oxford; Peter C. North, both of Royston; Michael B. Tyers, Welwyn, all of England

[73] Assignee: Glaxo Group Limited, London, England

[21] Appl. No.: 934,307

[22] Filed: Aug. 25, 1992

Related U.S. Application Data

[63] Continuation of Ser. No. 800,982, Dec. 2, 1991, abandoned, which is a continuation of Ser. No. 698,902, May 13, 1991, abandoned, which is a continuation of Ser. No. 538,939, Jun. 15, 1990, abandoned, which is a continuation of Ser. No. 400,345, Aug. 31, 1989, abandoned.

[30] Foreign Application Priority Data

Sep. 1, 1988 [GB] United Kingdom ............... 8820653

[51] Int. Cl.$^5$ .......................................... A61K 31/415
[52] U.S. Cl. .................................................. 514/397
[58] Field of Search ........................................ 514/397

[56] References Cited

U.S. PATENT DOCUMENTS

| | | | |
|---|---|---|---|
| 4,808,581 | 2/1989 | Oxford et al. | 514/397 |
| 4,835,173 | 5/1989 | Tyers | 514/397 |
| 4,859,662 | 8/1989 | Coates et al. | 514/397 |

FOREIGN PATENT DOCUMENTS 2193633  2/1988  United Kingdom.

*Primary Examiner*—S. J. Friedman
*Attorney, Agent, or Firm*—Bacon & Thomas

[57] ABSTRACT

The invention relates to the use of compounds of formula (I)

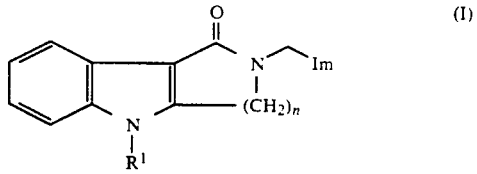

(I)

wherein Im represents an imidazolyl group of formula:

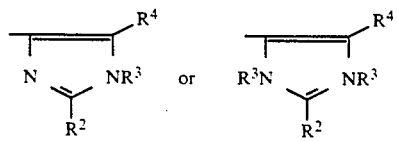

and $R^1$ represents a hydrogen atom or a group selected from $C_{1-6}$alkyl, $C_{3-6}$alkenyl, $C_{3-10}$alkynyl, $C_{3-7}$cycloalkyl, $C_{3-7}$cycloalkyl$C_{1-4}$alkyl, phenyl, phenyl$C_{1-3}$alkyl, phenylmethoxymethyl, phenoxyethyl, phenoxymethyl, —$CO_2R^5$, —$COR^5$, —$CONR^5R^6$ or —$SO_2R^5$ (wherein $R^5$ and $R^6$, which may be the same or different, each represents a hydrogen atom, a $C_{1-6}$alkyl or $C_{3-7}$cycloalkyl group, or a phenyl or phenyl$C_{1-4}$alkyl group, in which the phenyl group is optionally substituted by one or more $C_{1-4}$alkyl, $C_{1-4}$alkoxy or hydroxy groups or halogen atoms, with the proviso that $R^5$ does not represent a hydrogen atom when $R^1$ represents a group —$CO_2R^5$ or —$SO_2R^5$);
one of the groups represented by $R^2$, $R^3$ and R4 is a hydrogen atom or a $C_{1-6}$alkyl, $C_{3-7}$cycloalkyl, $C_{3-6}$alkenyl, phenyl or phenyl$C_{1-3}$alkyl group, and each of the other two groups, which may be the same or different, represents a hydrogen atom or a $C_{1-6}$ alkyl group;
and n represents 2 or 3, and physiologically acceptable salts and solvates thereof for the manufacture of a medicament for the treatment of depression.

15 Claims, No Drawings

MEDICAMENTS

This application is a continuation of application Ser. No. 07/800,982, filed Dec. 2, 1991, now abandoned, which is a continuation of application Ser. No. 07/698,902, filed May 13, 1991, now abandoned, which is a continuation of application Ser. No. 07/538,939, filed Jun. 15, 1990, now abandoned, which is a continuation of application Ser. No. 07/400,345, filed Aug. 31, 1989, now abandoned.

This invention relates to a further medical use for a group of heterocyclic compounds and pharmaceutical compositions containing them. In particular it relates to the use of certain lactam derivatives in the treatment of depression.

Compounds which are antagonists of 5-HT at 5-HT$_3$ receptors have been described previously for use in the treatment of depression in, for example, published European Patent Applications Nos. 276559 and 278173, and in German Offenlegungsschrift No. 3740352.

The present invention relates to the use, in this indication, of a particular group of compounds which are antagonists of 5-HT at 5-HT$_3$ receptors, as defined by the general formula (I).

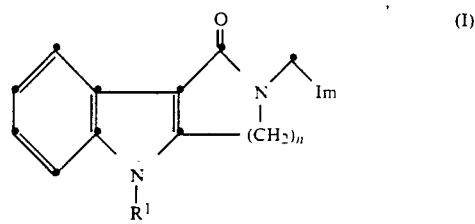

In the above formula Im represents an imidazolyl group of formula:

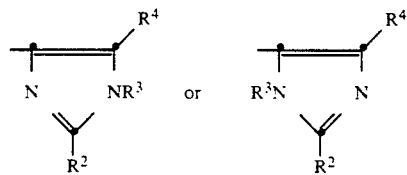

and $R^1$ represents a hydrogen atom or a group selected from $C_{1-6}$alkyl, $C_{3-6}$alkenyl, $C_{3-10}$alkynyl, $C_{3-7}$cycloalkyl, $C_{3-7}$cycloalkyl$C_{1-4}$ alkyl, phenyl, phenyl$C_{1-3}$alkyl, phenylmethoxymethyl, phenoxyethyl, phenoxymethyl, $-CO_2R^5$, $-COR^5$, $-CONR^5R^6$ or $-SO_2R^5$ (wherein $R^5$ and $R^6$, which may be the same or different, each represents a hydrogen atom, a $C_{1-6}$ alkyl or $C_{3-7}$ cycloalkyl group, or a phenyl or phenyl$C_{1-4}$alkyl group, in which the phenyl group is optionally substituted by one or more $C_{1-4}$ alkyl, $C_{1-4}$ alkoxy or hydroxy groups or halogen atoms, with the proviso that $R^5$ does not represent a hydrogen atom when $R^1$ represents a group $-CO_2R^5$ or $-SO_2R^5$);
one of the groups represented by $R^2$, $R^3$ and $R^4$ is a hydrogen atom or a $C_{1-6}$alkyl, $C_{3-7}$cycloakyl, $C_{3-6}$alkenyl, phenyl or phenyl$C_{1-3}$alkyl group, and each of the other two groups, which may be the same or different, represents a hydrogen atom or a $C_{1-6}$ alkyl group;
and n represents 2 or 3.

Suitable physiologically acceptable salts of the compounds of general formula (I) include acid addition salts formed with organic or inorganic acids for example, hydrochlorides, hydrobromides, sulphates, alkyl- or arylsulphonates (e.g. methanesulphonates or p-toluenesulphonates), phosphates, acetates, citrates, succinates, tartrates, fumarates and maleates. The solvates may, for example, be hydrates.

Compounds defined by the general formula (I) are the subject of published European Patent Application No. 306323, which was unpublished at the priority date of the present application.

The compounds of formula (I) are potent and selective antagonists of 5-hydroxytryptamine (5-HT) at 'neuronal' 5-HT receptors of the type located on terminals of primary afferent nerves. Receptors of this type are now designated as 5-HT$_3$ receptors and are also present in the central nervous system. 5-HT occurs widely in the neuronal pathways in the central nervous system and disturbance of these 5-HT containing pathways is known to alter behavioural syndromes such as mood, psychomotor activity, appetite and memory.

The potent and selective antagonism of 5-HT at 5-HT$_3$ receptors by compounds for use according to the invention has been demonstrated by their ability to inhibit 3-(5-methyl-1H- imidazol-4-yl)-1-[1-(methylt$_3$)-1H-indol-3-yl]-1-propanone binding in rat entorhinal cortex homogenates (following the general procedure described by G. Kilpatrick et al. in Nature, 1987, 330, 746), and/or by their ability to inhibit the 5-HT-induced depolarisation of the rat isolated vagus nerve preparation.

Compounds which are antagonists of 5-HT at 5-HT$_3$ receptors, such as the compounds of formula (I), are of use in the treatment of a human or animal subject suffering from anxiety, a psychotic disorder such as schizophrenia, or nausea and vomiting. The compounds are also useful in the treatment of gastric stasis; symptoms of gastrointestinal dysfunction such as occur with dyspepsia, peptic ulcer, reflux oesophagitis, flatulence and irritable bowel syndrome; migraine; and pain.

We have now found that the compounds of formula (I) and their physiologically acceptable salts and solvates, may be used in the treatment of depression.

Accordingly the invention provides a method of treatment of a human or animal subject suffering from depression, which comprises administering to a human or animal subject an effective amount of a compound of formula (I) or a physiologically acceptable salt or solvate thereof. The treatment of humans is particularly important.

References in this specification to treatment include prophylactic treatment as well as the acute alleviation of symptoms.

The use of all optical isomers of compounds of general formula (I) and their mixtures including the racemic mixtures thereof, and all the geometric isomers of compounds of formula (I), is embraced by the invention.

A particular group of compounds of formula (I) for use according to the invention is that wherein $R^1$ represents a hydrogen atom or a group selected from $C_{1-6}$ alkyl, $C_{3-6}$ alkenyl, $C_{3-10}$ alkynyl, $C_{3-7}$cycloalkyl, $C_{3-7}$cycloalkyl$C_{1-4}$ alkyl, phenyl or phenyl$C_{1-3}$ alkyl (n and Im being as defined in formula (I)).

A preferred group of compounds of formula (I) for use according to the invention is that wherein $R^1$ represents a hydrogen atom or a $C_{1-4}$ alkyl, $C_{3-4}$alkenyl, $C_{3-}$ 4alkynyl, $C_{5-6}$cycloalkyl, $C_{5-6}$cycloalkylmethyl, phenyl$C_{1-2}$ alkyl, phenylmethoxymethyl, N,N-di$C_{1-3}$alkylcarboxamido or $C_{1-3}$alkylsulphonyl group; $R^2$ represents a hydrogen atom; and $R^3$ and $R^4$ each represent a hydrogen atom or a $C_{1-3}$ alkyl group.

A particularly preferred group of compounds of formula (I) for use according to the invention is that wherein $R^1$ represents a methyl, n-propyl, prop-2-ynyl, cyclopentyl, cyclopentylmethyl, benzyl or N, N,dimethylcarboxamido group; $R^2$ and $R^3$ each represent a hydrogen atom; and $R^4$ represents a methyl group.

Within the above preferred and particularly preferred groups of compounds, an especially important group of compounds is that in which n represents 2.

Preferred compounds for use according to the invention are:

2,3,4,5-tetrahydro-5-(phenylmethyl)-2-[(5-methyl-1H-imidazol-4-yl)methyl]-1H-pyrido[4,3-b]indol-1-one;

5-cyclopentyl-2,3,4,5-tetrahydro-2-[(5-methyl-1H-imidazol-4-yl)methyl]-1H-pyrido[4,3-b]indol-1-one;

2,3,4,5-tetrahydro-2-[(5-methyl-1H-imidazol-4-yl)methyl]-5-propyl-1H-pyrido[4,3-b]indol-1-one;

5-(cyclopentylmethyl)-2,3,4,5-tetrahydro-2-[(5-methyl-1H-imidazol-4-yl)methyl]-1H-pyrido[4,3-b]indol-1-one;

3,4,5,6-tetrahydro-6-methyl-2-[(5-methyl-1H-imidazol-4-yl)methyl]azepino[4,3-b]indol-1(2H)-one;

2,3,4,5-tetrahydro-N,N-dimethyl-2-[(5-methyl-1H-imidazol-4-yl)methyl]-1-oxo-5H-pyrido[4,3-b]indole-5-carboxamide;

2,3,4,5-tetrahydro-2-[(5-methyl-1H-imidazol-4-yl)methyl]-5-(2-propynyl)-1H-pyrido[4,3-b]indol-1-one;

and their physiologically acceptable salts and solvates.

A particularly preferred compound for use according to the invention is 2,3,4,5-tetrahydro-5-methyl-2-[(5-methyl-1H-imidazol-4-yl)methyl]-1H-pyrido[4,3-b]indol-1-one and its physiologically acceptable salts and solvates. Preferred salts of this compound are the hydrochloride and maleate, of which the hydrochloride is particularly preferred.

In a further aspect, the invention provides a pharmaceutical composition which comprises an effective amount of a compound of formula (I) or a physiologically acceptable salt or solvate (e.g. hydrate) thereof, for use in human or veterinary medicine, particularly human medicine, for the treatment of depression.

In a yet further aspect, the invention provides for the use of a compound of formula (I) or a physiologically acceptable salt or solvate thereof, for the manufacture of a medicament for the treatment of depression.

Pharmaceutical compositions for use in accordance with the present invention may be formulated in conventional manner using one or more physiologically acceptable carriers of excipients.

Thus the compounds of formula (I) and their physiologically acceptable salts and solvates may be formulated for oral, buccal, parenteral, rectal or transdermal administration or in a form suitable for administration by inhalation or insufflation (either through the mouth or the nose). Oral administration is preferred.

For oral administration, the pharmaceutical compositions may take the form of, for example, tablets or capsules prepared by conventional means with pharmaceutically acceptable excipients such as binding agents (e.g. pregelatinised maize starch, polyvinylpyrrolidone or hydroxypropyl methylcellulose); fillers (e.g. lactose, microcrystalline cellulose or calcium hydrogen phosphate); lubricants (e.g. magnesium stearate, talc or silica); disintegrants (e.g. potato starch or sodium starch glycollate); or wetting agents (e.g. sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g. sorbitol syrup, cellulose derivatives or hydrogenated edible fats); emulsifying agents (e.g. lecithin or acacia); non-aqueous vehicles (e.g. almond oil, oily esters, ethyl alcohol or fractionated vegetable oils); and preservatives (e.g. methyl or propyl-p-hydroxybenzoates or sorbic acid). The preparations may also contain buffer salts, flavouring, colouring and sweetening agents as appropriate.

Preparations for oral administration may be suitably formulated to give controlled release of the active compound.

For buccal administration the compositions may take the form of tablets or lozenges formulated in conventional manner.

The compounds of formula (I) may be formulated for parenteral administration by injection e.g. by bolus injection or continuous infusion. Formulation for injection may be presented in unit dosage form e.g. in ampoules or in multi-dose containers, with an added preservative. The compositions may take such forms as suspensions, solutions or emulsions in oily or aqueous vehicles, and may contain formulatory agents such as suspending, stabilising and/or dispersing agents. Alternatively, the active ingredient may be in powder form for constitution with a suitable vehicle, e.g. sterile pyrogen-free water, before use.

The compounds of formula (I) may also be formulated in rectal compositions such as suppositories or retention enemas, e.g. containing conventional suppository bases such as cocoa butter or other glycerides.

In addition to the formulations described previously, the compounds may also be formulated as depot preparations. Such long acting formulations may be administered by implantation (for example subcutaneously, transcutaneously or intramuscularly) or by intramuscular injection. Thus, for example, the compounds of formula (I) may be formulated with suitable polymeric or hydrophobic materials (for example as an emulsion in an acceptable oil) or ion exchange resins, or as sparingly soluble derivatives, for example, as a sparingly soluble salt.

A proposed dose of a compound of formula (I) for use according to the invention for administration to man (of approximately 70 kg body weight) is 0.001 to 100 mg, for example 0.01 to 50 mg, of the active ingredient per unit dose, expressed as the weight of free base. A preferred dose of active ingredient per unit dose is 0.001 to 10 mg. The unit dose may be administered, for example, 1 to 4 times per day. The dose will depend on the route of administration. It will be appreciated that it may be necessary to make routine variations to the dosage depending on the age and weight of the patient as well as the severity of the condition to be treated.

Compounds of general formula (I) and physiologically acceptable salts or solvates thereof, may be prepared by the methods described in published European Patent Application No. 306323.

The following examples illustrate the preparation of 2,3,4,5-tetrahydro-5-methyl-2-[(5-methyl-1H-imidazol-4-yl)methyl]-1H-pyrido[4,3-b]indol-1-one and its hydrochloride salt, covered by formula (I). Temperatures are in ° C. Thin layer chromatograpy (t.l.c.) was carried out on silica. Organic extracts were dried, where indicated, over magnesium sulphate or sodium sulphate.

EXAMPLE 1

2,3,4,5-Tetrahydro-5-methyl-2-[(5-methyl-1H-imidazol-4-yl)methyl]-1H-pyrido[4,3-b]indol-1-one A suspension of 2,3,4,5-tetrahydro-5-methyl-1H-pyrido[4,3-b]indol-1-one (400 mg) in dry dimethoxyethane (50 ml) was treated with sodium hydride (60% dispersion in oil; 100 mg), and the mixture was stirred at 60° under nitrogen for 6 h. 4-(Chloromethyl)-5-methyl-1-(triphenylmethyl)-1H-imidazole (474 mg) was added and the reaction mixture was stirred at 60° under nitrogen overnight. 2N Hydrochloric acid (10 ml) and water (10 ml) were then added, and the mixture was heated at reflux for 6 h. After cooling, the mixture was basified with 2N sodium hydroxide and the resulting mixture was extracted with ethyl acetate (2×50 ml). The combined, dried organic extracts were concentrated onto flash column chromatography (FCC) silica and purified by FCC eluting with dichloromethane:ethanol: 0.88 ammonia (150:8:1) to give the title compound (352 mg) as a solid, t.l.c. (dichloromethane:ethanol:0.88 ammonia 100:8:1) Rf 0.28. $^1$H-N.m.r. (DMSO-d$_6$): δ 2.2 (3H,s), 3.04 (2H,t), 3.62 (2H,t), 3.72 (3H,s). 4.53 (2H,s), 7.1–7.28 (2H,m), 7.43 (1H,s), 7.47–7.55 (1H,dd), 7.94–8.03 (1H,dd).

EXAMPLE 2

2,3,4,5-Tetrahydro-5-methyl-2-[(5-methyl-1-H-imidazol-4-yl)methyl]-1H-pyrido[4,3-b]indol-1-one hydrochloride 2,3,4,5-Tetrahydro-5-methyl-2-[(5-methyl-1H-imidazol-4-yl)methyl]-1H-pyrido[4,3-b]indol-1-one (1.00 g) was suspended in ethanol (40 ml) and concentrated hydrochloric acid (1.00 ml) was added. The mixture was warmed to 40° and charcoal (0.25 g) was added. The resulting suspension was stirred and warmed for 5 min. and then filtered. The filtrate was evaporated in vacuo to ca. 20 ml and was allowed to cool to 20°. Ether (40 ml) was added with stirring over 5 min., and the mixture was stored at 4° overnight. The resulting precipitate was filtered off, washed with ether (2×10 ml), dried in vacuo at room temperature for 2 h and then at 70° for 7 h to give the title compound (0.95 g), m.p. 288°–291°.

Analysis Found: C,61.4; H,5.8; N,16.7; Cl, 10.7; C$_{17}$H$_{18}$N$_4$O.HCl requires C,61.7; H,5.8; N,16.9; Cl, 10.7%

The following examples illustrate pharmaceutical formulations for use according to the invention, containing, as the active ingredient, 2,3,4,5-tetrahydro-5-methyl-2-[(5-methyl-1H-imidazol-1-yl)methyl]-1H-pyrido-[4,3-b]indol-1-one (Compound A) in the form of its free base or hydrochloride salt (1.124 g of the hydrochloride is equivalent to 1 g of the free base). Other physiologically acceptable salts and/or solvates of Compound A, and other compounds of formula (I) and their physiologically acceptable salts and/or solvates may be formulated in a similar manner.

TABLETS FOR ORAL ADMINISTRATION

Tablets may be prepared by the normal methods such as direct compression or wet granulation.

The tablets may be film coated with suitable film forming materials, such as hydroxypropyl methylcellulose, using standard techniques. Alternatively the tablets may be sugar coated.

Direct Compression

| (i) Tablet | mg/tablet |
| --- | --- |
| Compound A free base | 0.50 |
| Calcium Hydrogen Phosphate BP* | 87.25 |
| Croscarmellose Sodium NF | 1.80 |
| Magnesium Stearate BP | 0.45 |
| Compression weight | 90.00 |

*of a grade suitable for direct compression.

The active ingredient is passed through a 60 mesh sieve, blended with the calcium hydrogen phosphate, croscarmellose sodium and magnesium stearate. The resultant mix is compressed into tablets using a Manesty F3 tablet machine fitted with 5.5 mm, flat bevelled edge punches.

| (ii) Tablet | mg/tablet |
| --- | --- |
| Compound A hydrochloride | 0.562 |
| Microcystalline cellulose NF | 31.250 |
| Lactose (anhydrous) NF | 111.303 |
| Pregelatinised maize starch BP | 6.250 |
| Magnesium Stearate | 0.625 |
| Compression weight | 150.0 |

*of a grade suitable for direct compression.

The active ingredient is passed through a 60 mesh sieve, blended with the lactose, microcystalline cellulose, pregelatinised maize starch and magnesium stearate. The resultant mix is compressed into tablets using a suitable tablet machine fitted with 7.0 mm, normal concave punches.

| Sub-Lingual Tablet | mg/tablet |
| --- | --- |
| Compound A hydrochloride | 0.562 |
| Compressible Sugar NF | 63.938 |
| Magnesium Stearate BP | 0.5 |
| Compression Weight | 65.0 |

The active ingredient is sieved through a suitable sieve, blended with the excipients and compressed using suitable punches.

Tablets of other strengths may be prepared by altering either the ratio of active ingredient to excipients or the compression weight and using punches to suit.

Wet Granulation

| Conventional Tablet | mg/tablet |
| --- | --- |
| Compound A hydrochloride | 0.562 |
| Lactose BP | 152.938 |
| Starch BP | 30.000 |
| Pregelatinised Maize Starch BP | 15.000 |
| Magnesium Stearate BP | 1.500 |
| Compression Weight | 200.0 |

The active ingredient is sieved through a suitable sieve and blended with lactose, starch and pregelatinised maize starch. Suitable volumes of purified water are added and the powders are granulated. After drying, the granules are screened and blended with the magnesium stearate. The granules are then compressed into tablets using 8 mm diameter punches.

Tablets of other strengths may be prepared by altering the ratio of active ingredient to lactose or the compression weight and using punches to suit.

| Sub-Lingual Tablet | mg/tablet |
|---|---|
| Compound A hydrochloride | 0.562 |
| Mannitol BP | 58.438 |
| Hydroxypropylmethylcellulose | 5.000 |
| Magnesium Stearate BP | 1.000 |
| Compression Weight | 65.0 |

The active ingredient is sieved through a suitable sieve and blended with the mannitol and hydroxypropylmethylcellulose. Suitable volumes of purified water are added and the powders are granulated. After drying, the granules are screened and blended into tablets using suitable punches.

Tablets of other strengths may be prepared by altering the ratio of active ingredient to mannitol or the compression weight and punches to suit.

| CAPSULES | mg/capsule |
|---|---|
| Compound A hydrochloride | 0.562 |
| *Starch 1500 | 98.438 |
| Magnesium Stearate BP | 1.000 |
| Fill Weight | 100.0 |

*a form of directly compressible starch.

The active ingredient is sieved and blended with the excipients. The mix is filled into size No. 2 hard gelatin capsules using suitabled machinery. Other doses may be prepared by altering the fill weight an if necessary changing the capsule size to suit.

Syrup

This may be either a sucrose or sucrose free presentation.

| A. Sucrose Syrup | mg/5 ml dose |
|---|---|
| Compound A hydrochloride | 0.562 |
| Sucrose BP | 2750.0 |
| Glycerine BP | 500.0 |
| Buffer | |
| Flavour | |
| Colour | as required |
| Preservative | |
| Purified Water BP | to 5.0 ml |

The active ingredient, buffer, flavour, colour and preservative are dissolved in some of the water and the glycerine is added. The remainder of the water is heated to dissolve the sucrose and is then cooled. The two solutions are combined, adjusted to volume and mixed. The syrup is clarified by filtration.

| B. Sucrose-Free | mg/5 ml dose |
|---|---|
| Compound A hydrochloride | 0.562 |
| Hydroxypropylmethylcellulose USP (viscosity type 4000) | 22.5 |
| Buffer | |
| Flavour | |
| Colour | as required |

| B. Sucrose-Free | mg/5 ml dose |
|---|---|
| Preservative | |
| Sweetener | |
| Purified Water BP | to 5.0 ml |

The hydroxypropylmethylcellulose is dispersed in hot water, cooled and then mixed with an aqueous solution containing the active ingredient and the components of the formulation. The resultant solution is adjusted to volume and mixed. The syrup is clarified by filtration.

INJECTION FOR INTRAVENOUS ADMINISTRATION

| | mg/ml | |
|---|---|---|
| (i) | | |
| Compound A free base | 0.05 | 0.5 |
| Sodium Chloride BP | as required | as required |
| Water for Injection | 1.0 ml | 1.0 ml |
| (ii) | | |
| Compound A hydrochloride | 0.0562 | 0.562 |
| Sodium Chloride BP | as required | as required |
| Water for Injection BP to | 1.0 ml | 1.0 ml |

Sodium chloride may be added to adjust the tonicity of the solution and the pH may be adjusted, using acid or alkali, to that of optimum stability and/or facilitate solution of the active ingredient. Alternatively, suitable buffer salts may be used.

The solution is prepared, clarified and filled into appropriate size ampoules sealed by fusion of the glass. The injection is sterilised by heating in an autoclave using one of the acceptable cycles. Alternatively, the solution may be sterilised by filtration and filled into sterile ampoules under aseptic conditions. The solution may be packed under an inert atmosphere of nitrogen or other suitable gas.

SUPPOSITORY

| (i) Compound A free base | 0.5 mg |
|---|---|
| *Witepsol H15 to | 1.0 g |
| (ii) Compound A hydrochloride | 0.562 mg |
| *Witepsol H15 to | 1.0 g |

*Witepsol H15 is a proprietary grade of Adeps Solidus Ph. Eur.

A suspension of the active ingredient is prepared in the molten Witepsol and filled, using suitable machinery, into 1 g size suppository moulds.

We claim:

1. A method for the treatment of depression which comprises adminstering to a human or animal subject suffering from depression an effective amount for the treatment of said depression of a compound of formula (I)

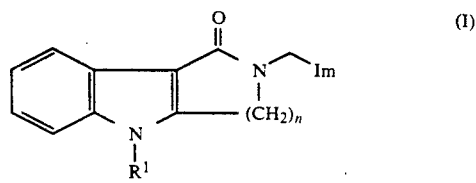

wherein Im represents an imidazolyl group of formula:

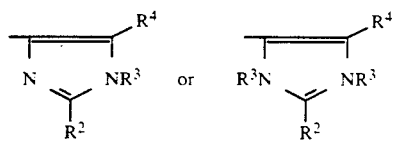

and R¹ represents a hydrogen atom or a group selected from $C_{1-6}$alkyl, $C_{3-6}$alkenyl, $C_{3-10}$alkynyl, $C_{3-7}$cycloalkyl, $C_{3-7}$cycloalkyl$C_{1-4}$alkyl, phenyl, phenyl$C_{1-3}$alkyl, phenylmethoxymethyl, phenoxyethyl, phenoxymethyl, —$CO_2R^5$, —$COR^5$, —$CONR^5R^6$ or —$SO_2R^5$ (wherein $R^5$ and $R^6$, which may be the same or different, each represents a hydrogen atom, a $C_{1-6}$alkyl or $C_{3-7}$cycloalkyl group, or a phenyl or phenyl$C_{1-4}$alkyl group, in which the phenyl group is optionally substituted by one or more $C_{1-4}$alkyl, $C_{1-4}$alkoxy or hydroxy groups or halogen atoms, with the proviso that $R^5$ does not represent a hydrogen atom when $R^1$ represents a group —$CO_2R^5$ or —$SO_2R^5$);

one of the groups represented by $R^2$, $R^3$ and $R^4$ is a hydrogen atom or a $C_{1-6}$alkyl, $C_{3-7}$cycloalkyl, $C_{3-6}$alkenyl, phenyl or phenyl$C_{1-3}$alkyl group, and each of the other two groups, which may be the same or different, represents a hydrogen atom or a $C_{1-6}$ alkyl group;

and n represents 2 or 3, or a physiologically acceptable salt or solvate thereof as the active ingredient.

2. A method according to claim 1 in which in the compound of formula (I) R¹ represents a hydrogen atom or a $C_{1-4}$alkyl, $C_{3-4}$alkenyl, $C_{3-4}$alkynyl, $C_{5-6}$cycloalkyl, $C_{5-6}$cycloalkylmethyl, phenyl$C_{1-2}$alkyl, phenylmethoxymethyl, N,N-di$C_{1-3}$alkylcarboxamido or $C_{1-3}$alkylsulphonyl group; R² represents a hydrogen atom; and R³ and R⁴ each represent a hydrogen atom or a $C_{1-3}$ alkyl group.

3. A method according to claim 1 in which in the compound of formula (I) R¹ represents a methyl, n-propyl, prop-2-ynyl, cyclopentyl, cyclopentylmethyl, benzyl or N,N-dimethylcarboxamido group; R² and R³ each represent a hydrogen atom; and R⁴ represents a methyl group.

4. A method according to claim 1 in which in the compound of formula (I), n is 2.

5. A method according to claim 1 in which said compound of formula (I) is selected from 2,3,4,5-tetrahydro-5-(phenylmethyl)-2-[(5-methyl-1H-imidazol-4-yl)-methyl]-1H-pyrido[4,3-b]indol-1-one;

5-cyclopentyl-2,34,5-tetrahydro-2-[5-methyl-1H-imidazol-4-yl)-methyl]-1H-pyrido[4,3-b]indol-1-one;

2,3,4,5-tetrahydro-2-[(5-methyl-1H-imidazol-4-yl)methyl]-5-propyl-1H-pyrido[4,3-b]indol-1-one;

5-(cyclopentylmethyl)-2,3,4,5-tetrahydro-2-[(5-methyl-1H-imidazol-4-yl)methyl]-1H-pyrido[4,3-b]indol-1-one;

3,4,5,6-tetrahydro-6-methyl-2-[(5-methyl-1H-imidazol-4-yl)methyl]-azepino[4,3-b]indol-1(2H)-one;

2,3,4,5-tetrahydro-N,N-dimethyl-2-[(5-methyl-1H-imidazol-4-yl)-methyl]-1-oxo-5H-pyrido[4,3-b]indole-5-carboxamide;

2,3,4,5-tetrahydro-2-[(5-methyl-1H-imidazol-4-yl)methyl]-5-(2-propynyl)-1H-pyrido[4,3-b]indol-1-one;

and physiologically acceptable salts and solvates thereof.

6. A method according to claim 1 in which said compound of formula (I) is administered in the form of a medicament in a form adapted for oral administration.

7. A method according to claim 1 in which said compound of formula (I) is administered in a unit dose of from 0.001 to 100 mg of the active ingredient.

8. A method according to claim 1 in which said compound of formula (I) is administered in a unit dose of from 0.001 to 10 mg of the active ingredient.

9. A method according to claim 2 in which in the compound of formula (I) R¹ is $C_{1-4}$ alkyl.

10. A method according to claim 9 in which in the compound of formula (I), n is 1.

11. A method for the treatment of depression which comprises administering to a human or animal subject suffering from depression an effective amount for the treatment of said depression of 2,3,4,5-tetrahydro-5-methyl-2-[(5-methyl-1H-imidazol-4-yl)methyl]-1H-pyrido[4,3-b]indol-1-one or a physiologically acceptable salt or solvate thereof.

12. A method according to claim 11 in which said compound is used in the form of its hydrochloride salt.

13. A method according to claim 11 in which said compound is administered in the form of a medicament in a form adapted for oral administration.

14. A method according to claim 11 in which said compound is administered in a unit dose of from 0.001 to 100 mg of the active ingredient.

15. A method according to claim 11 in which said compound is administered in a unit dose of from 0.001 to 10mg of the active ingredient.

* * * * *